US00PP27192P3

(12) United States Plant Patent
Robacker et al.

(10) Patent No.: US PP27,192 P3
(45) Date of Patent: Sep. 27, 2016

(54) ***VITEX NEGUNDO* PLANT NAMED 'LITTLE MADAME'**

(50) Latin Name: *Vitex negundo*
Varietal Denomination: Little Madame

(71) Applicant: University of Georgia Research Foundation, Inc., Athens, GA (US)

(72) Inventors: Carol D. Robacker, Peachtree City, GA (US); David A. Knauft, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 108 days.

(21) Appl. No.: 14/544,645

(22) Filed: Jan. 29, 2015

(65) Prior Publication Data

US 2016/0227689 P1 Aug. 4, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Klarquist Sparkman, LLP

(57) ABSTRACT

A new *vitex* plant named 'Little Madame' has violet blue flowers with a blotch of white on the anterior lip, has a compact form, a short internode length with nodes often having multiple branches. 'Little Madame' has mostly three to five leaflets and leaf margins that vary from entire to jagged.

5 Drawing Sheets

Genus and species: *Vitex negundo.*

Varietal denomination: The new *Vitex negundo* claimed is of the cultivar denominated 'Little Madame'.

BACKGROUND OF THE INVENTION

The present invention relates to a new and distinct cultivar of *Vitex negundo* hereinafter referred to by the varietal domination 'Little Madame'.

Pedigree and history: Under the direction of David Knauft, seeds from *Vitex negundo* 'Heterophylla' were irradiated with 3krad gamma radiation in 2006. These seeds were planted in a cultivated area in Watkinsville, Ga. in 2007. The new plant was selected from plants growing from these seeds and was initially called Vhet-3krad, seedling 1. This selected plant was asexually propagated via stem cuttings in Watkinsville, Ga., and was transferred to Carol Robacker's breeding program in 2009. The new variety was renamed Vhet-3kr' and subsequently renamed as 'Little Madame'. Three asexually propagated progeny of the new variety were planted in a field plot (randomized block design) in Griffin, Ga. (zone 8a) in June 2009. Plants of the new variety have been evaluated for five years at this site. One of the three progeny broke during planting, and never fully recovered. An additional three asexually propagated plants of the new variety were planted into the Griffin, Ga. field plot in the Spring of 2012. These plants have grown well, and appear to have vigor and other, characteristics like the plants from the 2009 planting. On Nov. 1, 2011, 52 rooted liners of the new plant were shipped to a company in Bonsall, Calif. for evaluation.

Height and width data has been collected annually. Cold damage was assessed each spring. Mean panicle length and number of panicles per compound panicle were counted each summer. First bloom and re-bloom dates were noted each year. Data was collected on leaf yellowing, leaf drop, and leaf spot in July, August and September of each year.

'Little Madame' has been grown in an irrigated field plot in Griffin, Ga. Plants have been fertilized annually in the spring. Height after five summer's growth is about 2.1 m. Stems are R.H.S. (Royal Horticultural Society Colour Chart, 2007) yellow-green RHS 146C the first year, becoming grey-brown RHS 199D the second year, round, and covered with very short curved hairs.

The trunk color is grey-brown RHS 199C. Exfoliation was not seen. Leaves emerge with a yellow-green RHS 144A upper surface, changing to a deeper yellow-green RHS 146C during the summer, and becoming lighter yellow-green RHS 146B in the fall. Fall leaves also have streaks of greyed-orange RHS 177A. Lower leaf surface color is yellow-green RHS 144B at emergence, becoming greyed-green RHS 194C in summer and fall.

Leaves are palmately-compound, 7 cm long×5 cm wide, with three to five leaflets. Margins are entire or smooth with an occasional jagged edge, and with acuminate apices and bases. The upper leaf surface has occasional short curved hairs, though the margins have many short hairs. The lower leaf surface has scattered short curved hairs, while the veins have many short curved hairs with scattered longer hairs. Leaves are slightly waxy and dull. Venation is simple. Leaf arrangement on stems is opposite.

Flower buds are violet RHS 85B with a dark violet RHS N88A blotch at the tip. Flowers occur in an elongated compound panicle, with a typical length of 8 cm. At emergence, flower petals are dark violet RHS N88A. At full bloom, flower petals are violet-blue RHS 94B with blotches of darker violet-blue RHS 94A on the anterior lip. The anterior lip also has a blotch of white RHS N155B. The peduncle is grayed-green RHS 194B. The number of individual flowers per inflorescence ranges from 25 to 53. Petals are 6 mm×3 mm. Sepals are greyed-green RHS 194C on the lower surface (the upper surface is not apparent). Anthers are dark violet RHS 86A with filaments light purple RHS 76B.

SUMMARY OF THE INVENTION

The following characteristics have been consistently observed in the original plant of this new variety and in asexually propagated progeny grown from cuttings and, to the best knowledge of the inventors, their combination forms the unique characteristics of 'Little Madame' as a new and distinct cultivar. Asexual propagation by cuttings has proven that these characteristics are firmly fixed in succeeding asexually propagated generations. As apparent from Tables 1-7 below, the combination of unique characteristics comprise:

1. Short height;
2. Compact form;
3. Short internode length;
4. Multiple branches at nodes;
5. Typically three to five leaflets;
6. Leaf margins vary from entire to jagged. Flower clusters that are of a relatively small diameter;
7. Typically two to four secondary panicles; and
8. Minimal leaf drop.

Comparison to standard: 'Little Madame' is an unusual dark purple *vitex* as compared to the standard *V. negundo* 'Heterophylla' (unpatented). All of the plants of the new variety were propagated from shoot cuttings, rooted and grown in one-gallon containers before being planted into the field. 'Little Madame' was planted into a field plot in Griffin in June 2009 (three plants), and another three plants were planted in June 2012. 'Heterophylla' was planted into the same field plot in June 2011. Data given in the Tables 1-7 below are based on two plants of 'Little Madame' that were planted in 2009 and one plant of 'Heterophylla'.

Comparison. Height and width were measured annually. 'Little Madame' is smaller than 'Heterophylla' and has a denser, more compact form (Table 1, FIG. 1). Internodes are also shorter in 'Little Madame' than 'Heterophylla', and multiple branches occur at nodes of 'Little Madame', while 'Heterophylla' shows the typical *vitex* pattern of two shoots per node (Table 2, FIG. 2). Foliage is also remarkably different. Both cultivars have palmately compound leaves, but 'Little Madame' has three to five leaflets while 'Heterophylla has five leaflets. The margins of the leaves of 'Little Madame' are entire or jagged, while those of 'Heterophylla' are lobed (Table 3, FIGS. 3 and 4).

In 2012, 'Little Madame' began flowering at the same time as 'Heterophylla'. However, in 2013, 'Little Madame' bloomed one week later than 'Heterophylla' (Table 4). The selection 'Little Madame' bloomed from June through August, with flowers in September in most years in Georgia as well. 'Heterophylla' shows a similar pattern, but with a tendency for re-bloom in August and September in Georgia, rather than July (Table 5). Panicles on 'Little Madame' are generally shorter in length than 'Heterophylla', though much variation occurs among panicles. The diameter of individual flower clusters on the panicles is also smaller on 'Little Madame' than 'Heterophylla'. The number of sub-panicles ranges from two to four on 'Little Madame' versus two to six on 'Heterophylla'. (Table 6, FIG. 5). Both 'Little Madame' and 'Heterophylla' have dark violet-blue flower color, N89C and N89D, respectively (FIG. 5).

No cold damage was observed on 'Little Madame' in any year (2010 through 2013) in Griffin, Ga. (zone 8a). 'Heterophylla' also had no cold damage, though a leaf spot was evident in both 2012 and 2013. 'Little Madame' showed no leaf spot or other disease at any time. Plants were rated for leaf yellowing and leaf drop in July through September of 2012 and 2013. Minor leaf yellowing was observed in most months for 'Little Madame', but leaf drop was minimal to none for most months (Table 7). 'Heterophylla' had minor to moderate yellowing in July and August, and moderate to severe yellowing in September. Moderate leaf drop occurred in most months (Table 7).

*Vitex negundo* is a deciduous shrub or small tree occasionally used in landscapes. This drought tolerant species is typically grown in cold hardiness zones 6 through 9. During cold winters in zone 6, plants of the species may die back to the ground, but will likely re-grow from the roots and produce a flowering shrub during the following summer, as flower buds are formed on new growth. Late spring freezes or cold mid-winter temperatures in zone 7 and 8 may also cause cold damage and dieback, but the plants recover and bloom during the summer.

'Little Madame' can be propagated vegetatively by stem cuttings.

In Tables 1-7 below, data for 'Little Madame' is based on two plants and the data for 'Heterophylla' is based on one plant. Numbers in parentheses are standard deviations.

TABLE 1

Height (H) and width (W) (cm) of *V. negundo* 'Little Madame', and 'Heterophylla' two, three and four years after planting in a field plot in Griffin, Georgia.

| Entry | Season 2 (H x W) | Season 3 | Season 4 |
|---|---|---|---|
| 'Little Madame' | 122 (30) × 177 (24) | 158 (29) × 231 (35) | 200 (0) × 260 (19) |
| 'Heterophylla' | 198 H × 219 W | 260 H × 322 W | 260 H × 396 W |

TABLE 2

Branching pattern of 'Little Madame' and 'Heterophylla'. Ten random samples were collected from each plant.

| Entry | Number of branches at a node | Internode length (mm) |
|---|---|---|
| 'Little Madame' | 5.8 (0.9) | 18 (7.1) |
| 'Heterophylla' | 2.0 (0) | 48 (9.2) |

TABLE 3

Description of foliage of 'Little Madame' and 'Heterophylla'

| Entry | Number of leaflets | Leaf margin |
|---|---|---|
| 'Little Madame' | Three to five | Entire or serrated |
| 'Heterophylla' | Five | Lobed |

TABLE 4

First bloom dates of 'Little Madame' and 'Heterophylla' grown in Griffin, Georgia.

| Entry | First bloom 2011 | First bloom 2012 | First bloom 2013 |
|---|---|---|---|
| 'Little Madame' | 5-30 | 5-14 | 6-17 |
| 'Heterophylla' | — | 5-14 | 6-10 |

TABLE 5

Repeat flowering in July, August, September and October in 2011, 2012, and 2013.

| Entry | Year | July | August | September | October |
|---|---|---|---|---|---|
| 'Little Madame' | 2011 | 2.5* | 3 | 3 | 0 |
| | 2012 | 2.5 | 3 | 0.5 | 0 |
| | 2013 | 3 | 3 | 0 | 0 |
| 'Heterophylla' | 2011 | 0 | 3 | 2.5 | 0 |
| | 2012 | 2.5 | 3 | 2.5 | 0.5 |
| | 2013 | 0 | 0.5 | 1 | 0 |

*Repeat flowering was rated using the following scale:
0 = no flowering;
1 = 10% full bloom;
2 = 20 to 30% full bloom;
3 = 40 to 50% full bloom;
4 = at least 60% full bloom.

TABLE 6

Panicle length, diameter and number of secondary peduncles per panicle, were based on ten random samples.

| Entry | Mean panicle length (cm) | Mean panicle diameter (cm) | Number of secondary peduncles/panicle |
|---|---|---|---|
| 'Little Madame' | 12.5 (1.9) | 1.2 (0.33) | Two to four |
| 'Heterophylla' | 15.1 (2.6) | 1.7 (0.30) | Two to six |

TABLE 7

Ratings of leaf yellowing and leaf drop in late summer of 2012 and 2013.

| | | Leaf yellowing* | | Leaf drop* | |
|---|---|---|---|---|---|
| Entry | Month | 2012 | 2013 | 2012 | 2013 |
| 'Little Madame' | July | 0.5 ± 0.7 | 0 ± 0 | 0.5 ± 0.7 | 0 ± 0 |
| | August | 1 ± 0 | 0.5 ± 0 | 0 ± 0 | 0 ± 0 |
| | September | 1 ± 0 | 1 ± 0 | 0 ± 0 | 1 ± 0 |
| 'Heterophylla' | July | 1 | 1 | 1 | 2 |
| | August | 2 | 1 | 2 | 1 |
| | September | 2 | 3 | 2 | 0 |

*Leaf yellowing and leaf drop were rated as follows:
0 = none observed;
1 = minor level
2 = moderate level;
3 = severe level.

BRIEF DESCRIPTION OF THE FIGURES

The accompanying colored photographic illustrations show the overall appearance and distinct characteristics of the new cultivar of *Vitex negundo*. The colors in the photographs are as close as possible with the photographic and printing technology utilized.

DETAILED BOTANICAL DESCRIPTION

Figure 1:
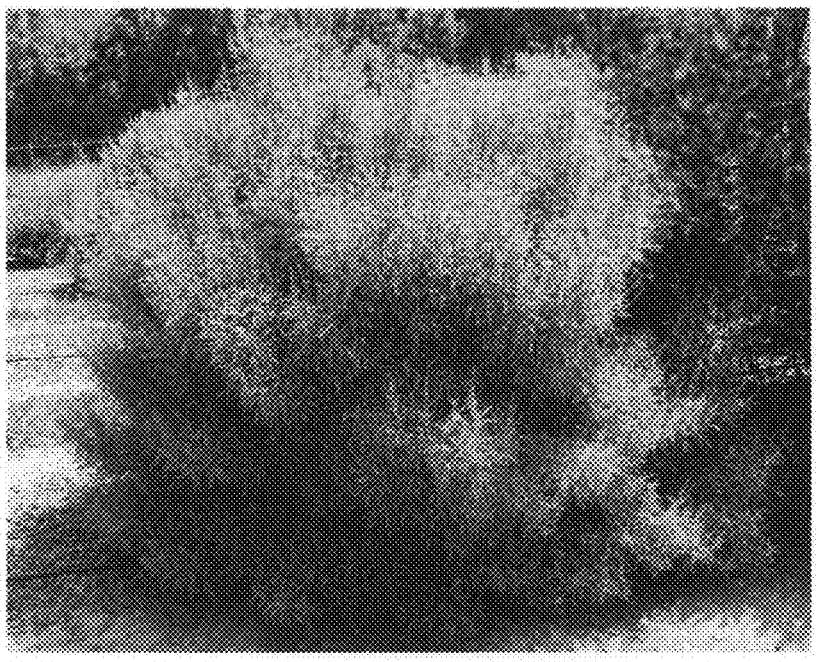
FIG. 1 is a photograph of the new variety 'Little Madame' (Top image) during flowering in Griffin, Ga. and a photograph of 'Heterophylla' (bottom). 'Little Madame' is smaller and more compact than 'Heterophylla.'
Figure 1:
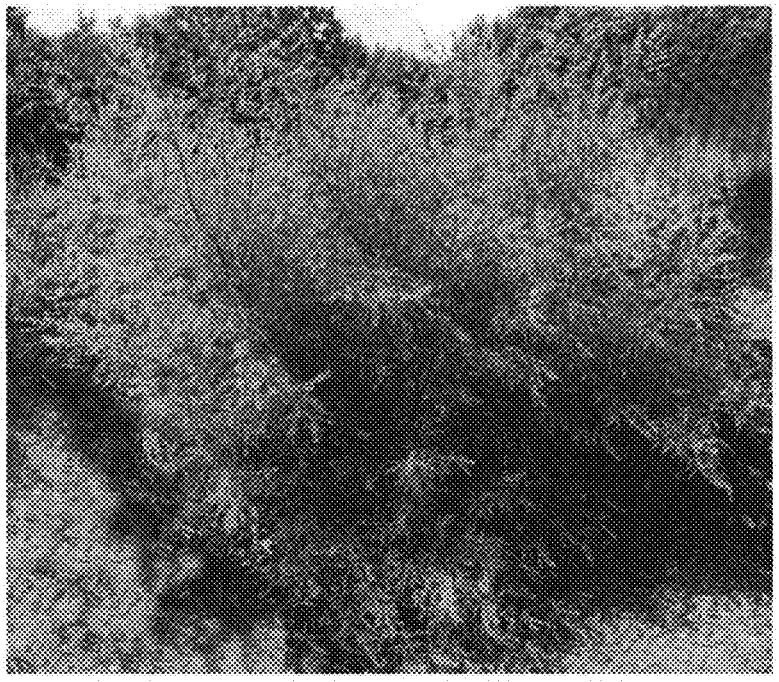
Figure 2:
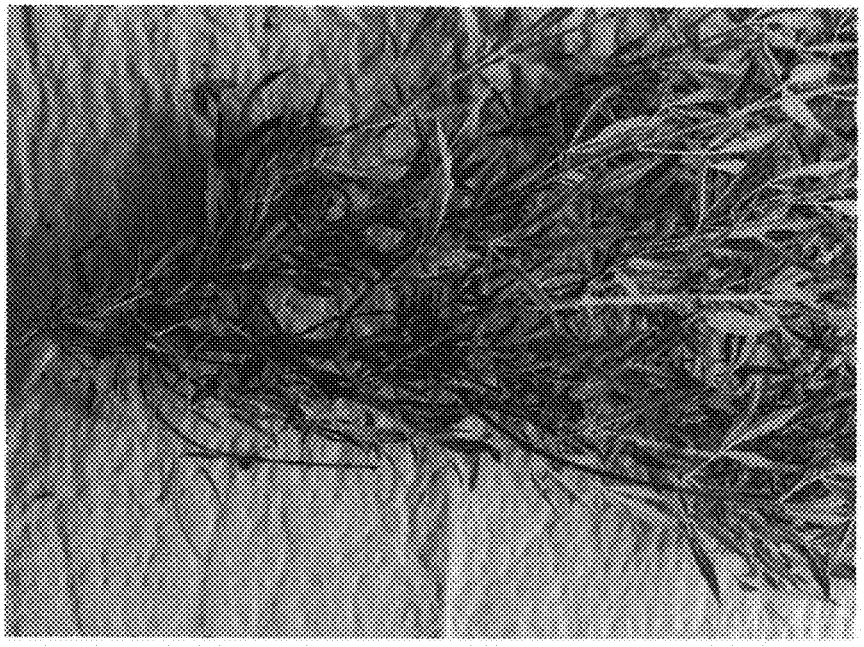
FIG. 2 shows the shorter internodes and increased branching of 'Little Madame' (top) compared to 'Heterophylla' (bottom).
Figure 2:
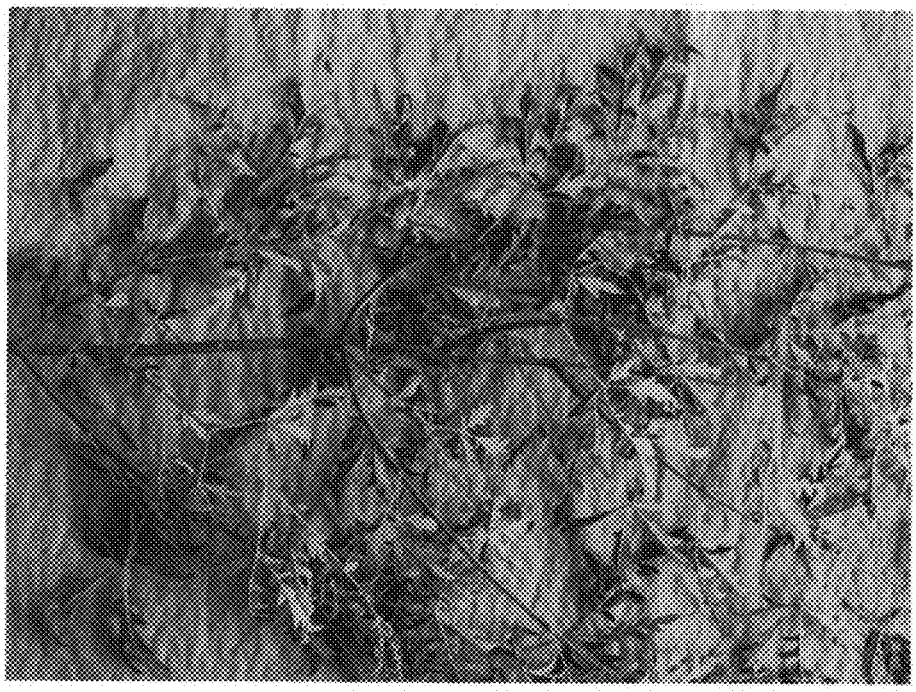
Figure 3:
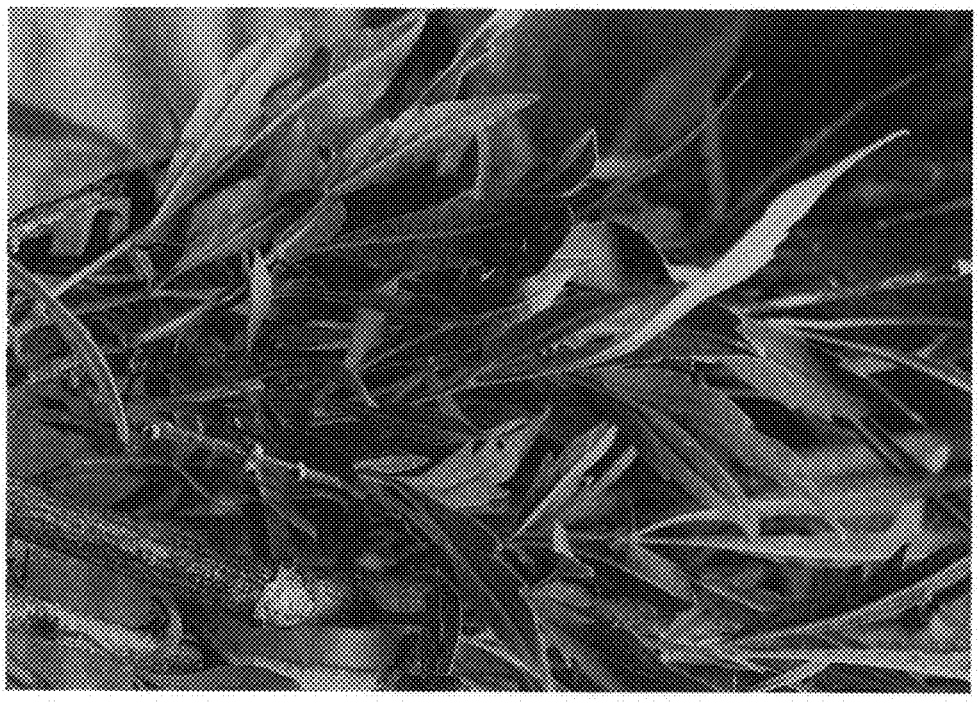
FIG. 3 shows the foliage variation of 'Little Madame'. Top photo shows serrated margins and the bottom shows entire margins. Leaflet number varies from three to five.
Figure 3:
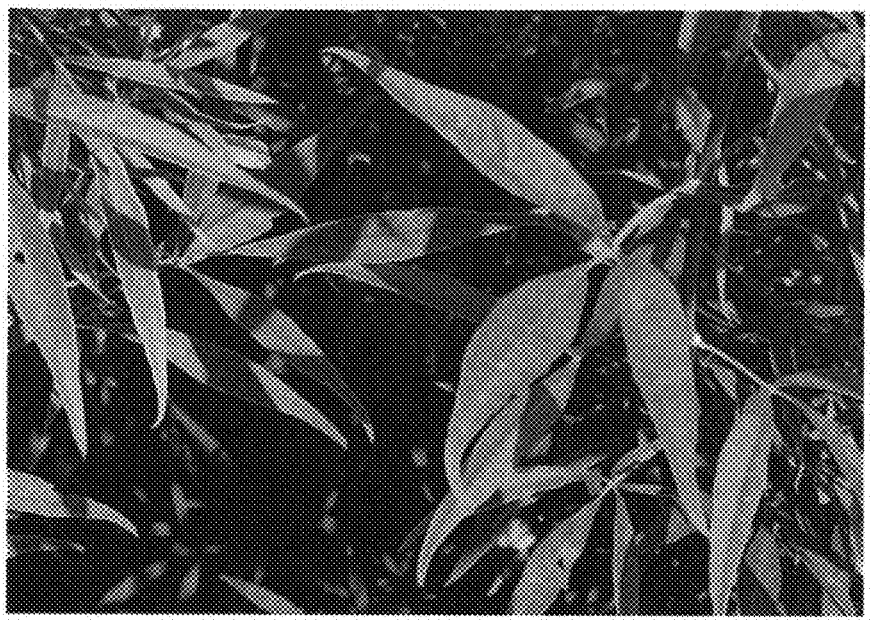
Figure 4:
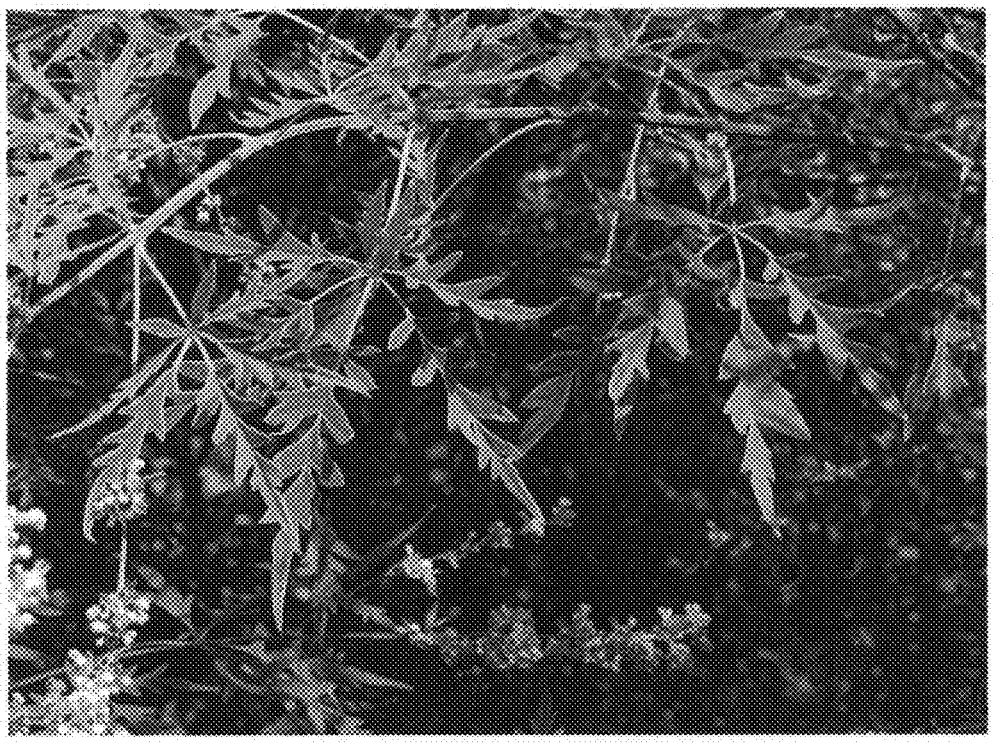
FIG. 4 shows the foliage of 'Heterophylla' showing five leaflets with lobed margins.
Figure 5:
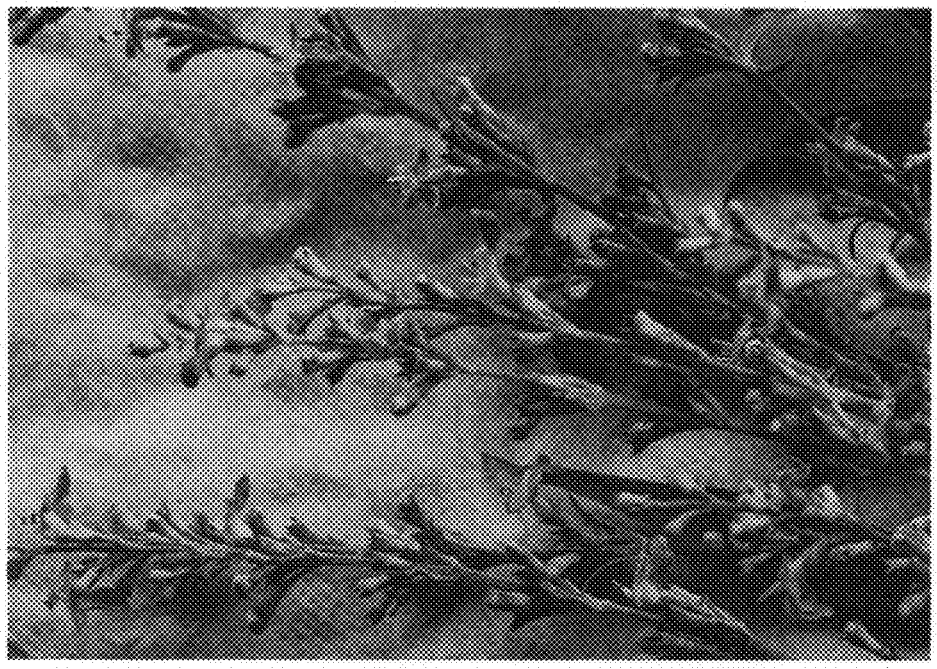
FIG. 5 shows the smaller flower clusters of 'Little Madame' (top) in comparison to the larger flower clusters of 'Heterophylla' (bottom). Both cultivars have similar flower colors.
Figure 5:
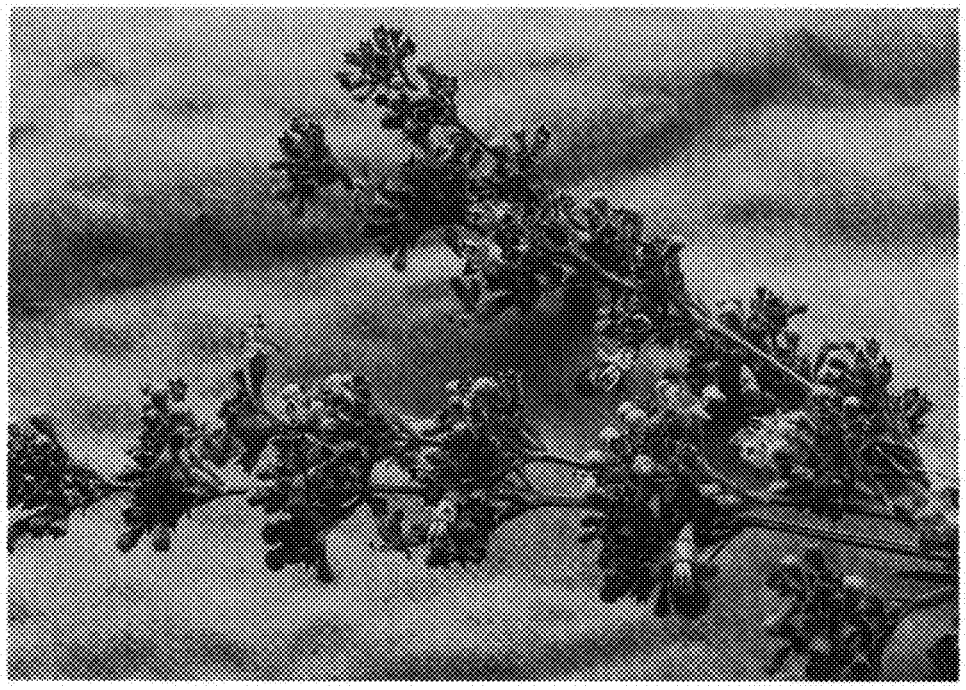

The following is a detailed description of the new 'Little Madame' cultivar. Data was collected in Griffin, Ga. from plants grown from cuttings and growing outdoors. 'Little Madame' has not been tested under all possible conditions, hence, phenotypic differences may be observed with variations in environmental conditions without any variance in genotype.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society (R.H.S.), London, England.

Parentage: Induced mutation of 'Heterophylla'.

Size: 210 cm tall by 306 cm wide, measured at highest and widest point, after five years growth. Size is reflective of habit, i.e., 2' by 3' is rounded to broad-rounded.

Habit: Broad rounded, upright.

Texture: Fine.

Stems:

*First year.*—Color: Yellow-Green RHS 146C. Diameter: 2-3 mm. Pubescence: covered in very short, curved hairs. Exfoliation: none. Shape: Round. Pith: Type: Solid. Diameter: 1.5 mm. Color: White RHS 155C. Odor: mild, spicy. Internode Length: approximately 2.5 cm.

*Second year.*—Color: Grey-Brown RHS 199D. Diameter: approximately 7 mm. Exfoliation: none.

Vegetative buds:

*Arrangement.*—Opposite.
*Type.*—Valvate.
*Size.*—1 mm×1 mm.
*Scale number.*—2.
*Scale color.*—Greyed-Orange RHS 165B.
*Position/disposition.*—45°.
*Number at node.*—2 or more.
*Pubescence.*—Tomentose.
*Shape.*—Round.

Leaf scar:

*Shape.*—Crescent.
*Vascular bundle traces.*—3, horizontal.
*Pubescence.*—Short hairs around perimeter.
*Position of bud.*—45° in leaf axil above vascular bundle.
*Color differentiation.*—Yellow-Green RHS 146C.
*Size.*—1×1 mm.

Trunk or large stems:

*Color.*—Grey-Brown RHS 199C.
*Size stem exfoliation begins on.*—None observed.
*Diameter.*—2 cm and greater.
*Texture.*—Mostly smooth.

Leaf:

*Color through seasons*.—Emerging dates — Late April to early May. Upper: Yellow-Green RHS 144A. Lower: Yellow-Green RHS 144B. Summer dates — mid July. Upper: Yellow-Green RHS 146C. Lower: Greyed-Green RHS 194C. Fall dates — September. Upper: Yellow-Green RHS 146B with Greyed-Orange RHS 177A. Lower: Greyed-Green RHS 194C.

*Mature size*.—Typical 7 cm×5 cm.

*Apex*.—Acuminate.

*Base*.—Acuminate.

*Margin*.—Mostly entire, occasionally jagged.

*Shape*.—Palmate, mostly 3 to 5 leaflets. Lobes: None. Shape: acutely elliptic. Sinuses: none.

*Vein color*.—Yellow-Green RHS 144B.

*Pubescence*.—Upper surface has occasional short curved hairs; margins have many short hairs; veins have many short curved hairs with scattered longer hairs.

*Arrangement on stem*.—Opposite.

*Venation*.—Simple.

*Texture*.—Thickness: 0.35 mm. Degree of waxiness of surfaces: slightly waxy, not shiny.

Petiole:

*Length*.—Approximately 2 cm.

*Shape*.—Slender, round.

*Color*.—Yellow-Green RHS 144A.

*Pubescence*.—Densely covered in short curved hairs.

*Diameter*.—0.6 mm.

Flower buds:

*Size* (*l*×*w*).—4 mm×1.5 mm.

*Color*.—Violet RHS 85B with Violet RHS N88A blotch at tip.

*Shape*.—Small teardrop.

*Pubescence*.—Densely covered in short hairs.

*Time of full maturity* (*first visible*).—Late spring, early June.

*Time range for showiness*.—Mid May through September.

Flower:

*Inflorescence*(*s*).—Type: compound panicle. Size (l×w): 8 cm×1.5 cm. Color: at emergence — Violet RHS N88A. full bloom — Violet-Blue RHS 94B with blotches of Violet-Blue RHS 94A on anterior lip; anterior also has blotch of White RHS N155B. fading — Violet-Blue RHS 94B with blotches of Violet-Blue RHS 94A on anterior lip; anterior also has blotch of White RHS N155B. Peduncle: Color: Greyed-Green RHS 194B. Pubescence: densely covered with short hairs. Number of individual flowers per inflorescence: 25-53.

*Petal*(*s*).—Size: 6 mm×3 mm. Shape: zygomorphic, gamopetalous, bilabiate. Apex: lobed, zygomorphic. Base: funnel. Margin: slightly curled. Pubescence: mostly glabrous inside, with hairs and anterior blotch (some are y-shaped); scattered hairs outside. Texture: mostly glabrous, very few glands. Color at peak of bloom: upper surface — Violet-Blue RHS 94B with blotches of Violet-Blue RHS 94A on anterior lip; anterior lip also has a blotch of White RHS N155B. lower surface — Violet RHS 85B. Pedicels: color (RHS) — Greyed-Green RHS 194B. pubescence — densely covered in short hairs. length — 1-2 mm.

*Sepal*(*s*).—Size (l×w): 3 mm×1 mm. Shape: united, slightly lobed. Apex: slightly lobed. Base: united, short tubular, small bracteoles present. Margin: smooth. Pubescence: covered in short hairs. Texture: hoary. Color at peak of bloom: upper surface — not reflexed — not visible. lower surfaces — Greyed-Green RHS 194C.

*Male reproductive structures*.—Number: 4. Anther: size (l×w) — 1 mm×0.5 mm. color — Violet RHS 86A. Filament: size (l×w) — 4 mm×0.5 mm. color — Purple RHS 76B. Pollen color — White RHS NN155D. Pubescence — smooth toward anthers, scattered hairs midway, becoming densely tufted at base.

*Female reproductive structures*.—Pistil: shape — tubular, bifid. size (l×w) — 4 mm×0.5 mm. position (superior, inferior, etc.) — superior. color (R.H.S.) — Purple RHS 76B. pubescence — thickly tufted hairs at base. Stigma: shape — round, bifid. color (R.H.S.) — White RHS 155C. pubescence — none. Style: length — approximately 3.5 mm. shape — tubular, forked at stigma (bifid). color (R.H.S.) — Purple RHS 76B. pubescence — sparse, tufted at base. Ovary: shape — round. number — 1. pubescence — many short hairs, numerous glands present.

Fruit:

*Type*.—Drupe-like.

*Size* (*l*×*w*).—2.5 mm×1.5 mm.

*Color*(*s*) *during ripening*.—Early — Yellow-Green RHS N144B (mid June). late — Brown RHS 200B.

*Shape*.—Globular.

*Number per infructescence*.—1.

*Pubescence*.—Scattered very short hairs, glands present on surface.

*Number of carpels*.—2.

*Persistence* (*effective period*).—Mid to late summer through fall into winter.

Seed:

*Shape*.—Globular.

*Size*.—2.5 mm×1.5 mm.

*Color*.—Brown RHS 200B when fully ripe.

*Number per locule per ovary per fruit*.—1.

*Germination capacity*.—Very low, sets few viable seeds.

*Pubescence*.—None.

What is claimed is:

1. A new and distinct cultivar of the *Vitex negundo* plant named 'Little Madame' substantially as illustrated and described herein.

* * * * *

'Little Madame'

'Heterophylla'

'Little Madame'

'Heterophylla'

'Little Madame'

'Little Madame'

'Heterophylla'

'Little Madame'

'Heterophylla'